United States Patent [19]

Sher

[11] Patent Number: 5,238,951
[45] Date of Patent: Aug. 24, 1993

[54] HETEROCYCLIC AMIDO PROSTAGLANDIN ANALOGS

[75] Inventor: Philip M. Sher, Plainsboro, N.J.

[73] Assignee: E. R. Squibb & Sons, Inc., Princeton, N.J.

[21] Appl. No.: 931,439

[22] Filed: Aug. 20, 1992

Related U.S. Application Data

[63] Continuation of Ser. No. 649,633, Feb. 1, 1991, abandoned.

[51] Int. Cl.$^5$ .................. C07D 493/08; A61K 31/41
[52] U.S. Cl. ............................ 514/364; 514/383; 548/131; 548/266.8
[58] Field of Search ............... 548/131, 266.8; 514/364, 383

[56] References Cited

U.S. PATENT DOCUMENTS 4,526,901 7/1985 Nakane .................. 514/469

FOREIGN PATENT DOCUMENTS 374952  6/1990 European Pat. Off. ........... 548/200
0391652 10/1990 European Pat. Off. .
0448274  9/1991 European Pat. Off. .

OTHER PUBLICATIONS

C. W. Thornber, Chemical Society Reviews, vol. 18, pp. 563-580 (1979).

*Primary Examiner*—Robert Gerstl
*Attorney, Agent, or Firm*—Timothy J. Gaul

[57] ABSTRACT

Prostaglandin analogs useful in treating thrombotic and vasospastic disease having the structural formula

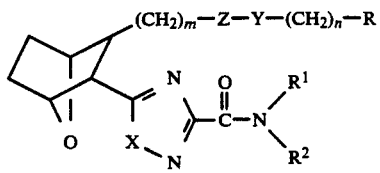

wherein:
m is 1, 2, or 3;
n is 0, 1, 2 or 3;
R is $CO_2R'$, $CH_2OH$, $CONHSO_2R_{hu\ 3}$, $CONHR^4$, or $—CH_2$-5-tetrazolyl;
R' is hydrogen, alkyl, or alkali metal;
X is O or NH;
Y is —O—, a single bond or vinylene, except that Y cannot be —O— when n is 0 and if Y is vinylene, then n=0;

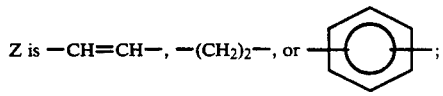

and the remaining symbols are as defined in the specification.

20 Claims, No Drawings

HETEROCYCLIC AMIDO PROSTAGLANDIN ANALOGS

This is a continuation of copending application Ser. No. 649,633 filed on Feb. 1, 1991 now abandoned.

FIELD OF THE INVENTION

This invention relates to prostaglandin analogs useful as thromboxane $A_2$ receptor antagonists.

BRIEF DESCRIPTION OF THE INVENTION

A compound of the formula

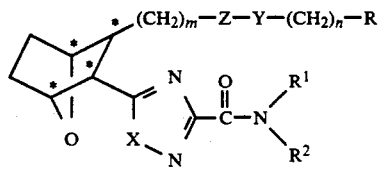

is a thromboxane $A_2$ (TXA$_2$) receptor antagonist or a combined thromboxane $A_2$ receptor antagonist/thromboxane synthetase inhibitor. Compound I is useful, for example, in treating thrombotic or vasospastic disease with good duration of action. In compound I and throughout this specification, the symbols above are defined as follows:

m is 1, 2, or 3;
n is 0, 1, 2 or 3;
R is $CO_2R'$, $CH_2OH$, $CONHSO_2R^3$, $CONHR^4$, or —$CH_2$-5-tetrazolyl;
R' is hydrogen, alkyl, or alkali metal;
X is O or NH;
Y is —O—, a single bond or vinylene, except that Y cannot be —O— when n is 0 and if Y is vinylene, then n=0;

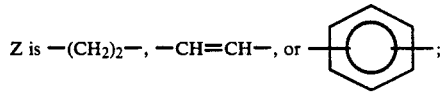

R' is hydrogen, alkyl, alkenyl, alkynyl, aralkyl, aryl, cycloalkyl, cycloalkylalkyl, cycloheteroalkyl, cycloheteroalkylalkyl, heteroaryl or heteroarylalkyl, or amide

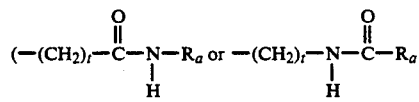

wherein t is 1 to 12 and $R_a$ is alkyl, aryl, cycloalkyl, or cycloalkylalkyl), each of $R^1$ being unsubstituted or optionally substituted with alkyl, aryl, cycloalkyl, or cycloalkylalkyl;
$R^2$ is hydrogen, alkyl, aryl, or aralkyl; or
$R^1$ and $R^2$ together with the nitrogen to which they are linked may form a 5- to 8-membered ring;
$R^3$ is alkyl, aryl or aralkyl; and
$R^4$ is hydrogen, alkyl, aryl, aryl or aralkyl.

Thus, the compounds of the invention include the following types of compounds, which are preferred:

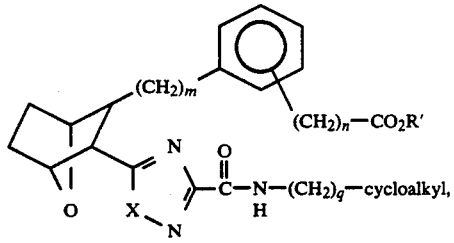

and

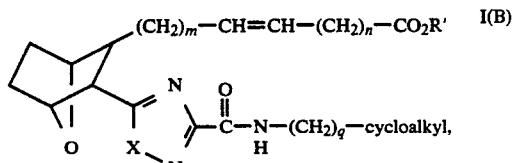

wherein X, R', and n are as defined above and q is an integer from 1 to 7. Most preferred are those compounds wherein R' is hydrogen, m is 1, n is 2, q is 4, and the cycloalkyl group is cyclohexyl.

DETAILED DESCRIPTION OF THE INVENTION

Definition of Terms

The term "alkyl" includes both straight and branched chain radicals of up to 12 carbons, preferably 1 to 4 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof and the like, which may be substituted with one or two trifluoromethyl, halo or hydroxyl groups.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl.

The term "aryl" or "Ar" refers to monocyclic or bicyclic aromatic groups containing from 6 to 10 carbons in the ring portion, such as phenyl and naphthyl, which may include 1 or 2 substituents on either the phenyl or naphthyl such as alkyl, trifluoromethyl, halogen (Cl, Br, I or F), alkoxy, arylalkoxy, hydroxy, alkylthio, alkylsulfinyl, alkylsulfonyl, phenylthio, phenylsulfinyl and/or phenylsulfonyl.

The term "aralkyl" refers to alkyl groups as discussed above having an aryl substituent, such as benzyl.

The terms "alkoxy" and "aralkoxy" refer to the above alkyl and aralkyl groups linked to an oxygen atom.

The term "halogen" or "halo" refers to chlorine, bromine, fluorine or iodine, with chlorine being preferred.

The term "alkenyl" as employed herein with respect to the $R^1$ substituent includes a carbon chain of up to 12 carbons, preferably 3 to 10 carbons, having at least one double bond, which will be separated from "N" by at least one saturated carbon moiety such as —$(CH_2)_q$— where q can be 1 to 14, such as 2-propenyl, 2-butenyl, 3-butenyl, 2-pentenyl, 4-pentenyl and the like, and may include a halogen substituent such as I, Cl, or F.

The term "alkynyl" as employed herein with respect to the $R^1$ substituent includes a carbon chain of up to 16 carbons, preferably 3 to 10 carbons, having at least one triple bond, which will be separated from "N" by at least one saturated carbon moiety such as $-(CH_2)_q-$ wherein q can be 1 to 14, such as 2-propynyl, 2-butynyl, 3-butynyl and the like.

The term "cycloheteroalkyl" as used herein as an $R^1$ substituent refers to 5-, 6- or 7-membered saturated rings that include 1 or 2 heteroatoms such as nitrogen, oxygen and/or sulfur, and which are linked to the "N" of the

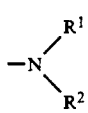

group through a carbon atom either beta or gamma to a heteroatom, such as

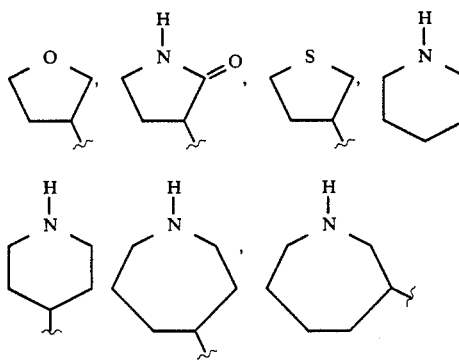

and the like.

The term "heteroaryl" or "heteroaromatic" as an $R^1$ substituent refers to 5- or 6-membered aromatic rings that include 1 or 2 heteroatoms such as nitrogen, oxygen or sulfur, which are not directly linked through a heteroatom to the "N" of the

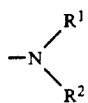

group, such as

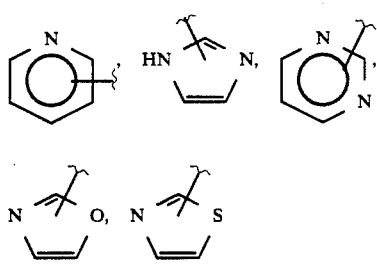

and the like.

The term "cycloheteroalkylalkyl" as used herein with respect to $R^1$ refers to 5-, 6- or 7-membered saturated rings that include 1 to 2 heteroatoms such as nitrogen, oxygen or sulfur, and are linked to the "N" of the

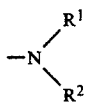

group through a $(CH_2)_x$ chain wherein x is 1 to 12, preferably 1 to 8, such as

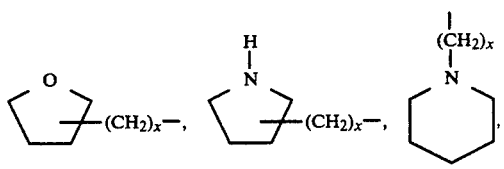

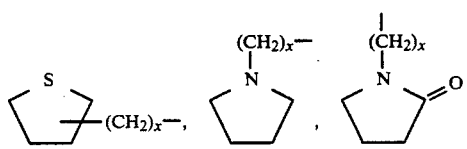

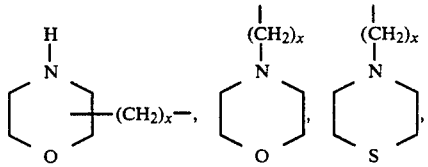

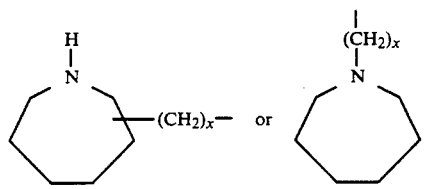

and the like.

The term "heteroarylalkyl" as used herein with respect to $R^1$ refers to 5-, 6- or 7-membered aromatic rings that include 1 to 4 nitrogen and/or 1 or 2 oxygen or sulfur atoms, and is linked to the "N" of the

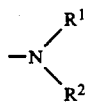

group through a $-(CH_2)_x-$ chain where x is 1 to 12, preferably 1 to 8, such

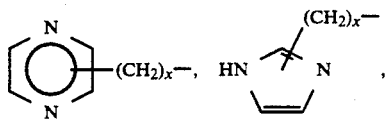

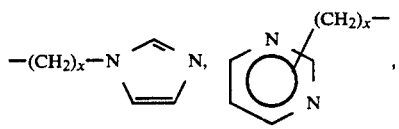

-continued

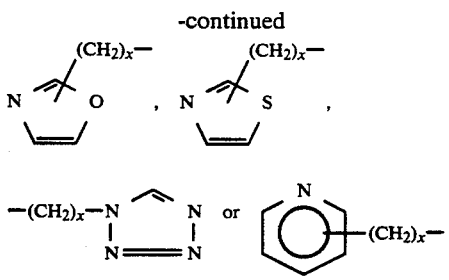

and the like.

Processes of Preparation

Compounds of the invention wherein Y is a single bond and X is N are prepared starting with bromophenylalkyl alcohol A

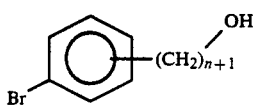

wherein n is 1, 2, 3 or 4. Compound A is treated with a protecting compound (e.g., t-butylchlorodiphenylsilane) in the presence of an amine base (e.g., triethylamine) and an inert solvent, employing conventional procedures, to form the protected bromophenylalkyl compound B

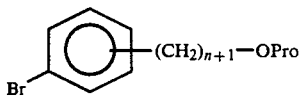

wherein Pro represents a protecting group. of protecting compounds suitable for use herein in reacting with bromophenalkyl alcohol A include but are not limited to

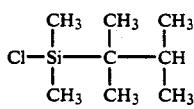

(chlorodimethylthexylsilane

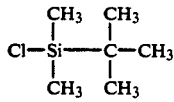

(chlorodimethyl-t-butylsilane)

or

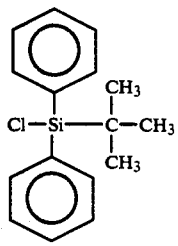

-continued (t-butylchlorodiphenylsilane) and the like.

The protected compound B then undergoes a metal-halogen exchange reaction by treatment with, for example, t-$C_4H_9Li$ or n-$C_4H_9Li$ in the presence of diethyl ether or tetrahydrofuran (THF) at about $-100°$ to about $0°$ C., or is preferably subjected to a Grignard reaction by treatment with magnesium in the presence of an inert organic solvent (e.g., THF or diethyl ether) and then is condensed with (exo)octahydro-5,8-epoxy-1H-benzopyran-3-ol or (exo)octahydro-4,7-epoxyisobenzofuran-1-ol (prepared as described in U.S. Pat. No. 4,143,054 or in Patel et al., "(exo,exo)-7-oxabicyclo[2.2.1] heptane-2,3-dimethanol, monoacyl ester, diacyl ester and enzymatic hydrolysis thereof", U.S. Ser. No. 629,780, filed Dec. 18, 1990) of the structure C

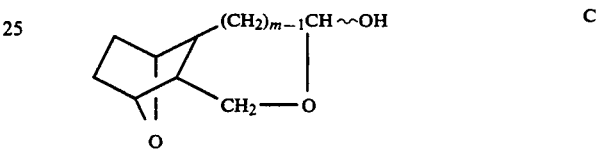

employing a molar ratio of C:B from about 1:2 to about 1:4, in the presence of an inert organic solvent such as THF at about $-78°$ to about $25°$ C. to form the condensed 7-oxabicycloheptane compound

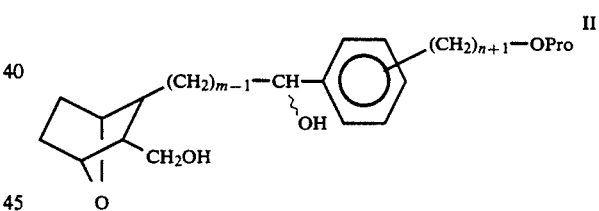

The condensed compound II is then subjected to hydrogenolysis by treatment with hydrogen in hydroxide on charcoal) in acetic acid or an inert organic solvent (e.g., ethyl acetate) to form the alcohol

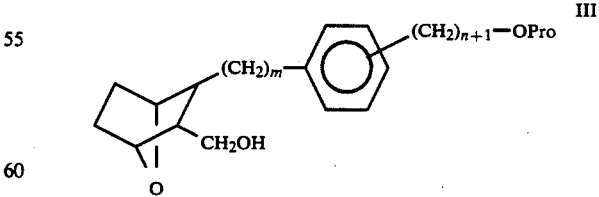

When the protecting group (Pro) in alcohol III is thexyldimethylsilyl or t-butyldimethylsilyl, alcohol III may be reacted with an acetylating agent (e.g., acetic anhydride) in the presence of pyridine and dimethylaminopyridine (DMAP) to form

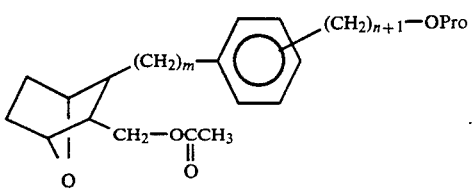

Acetylated compound IV is then reacted with Jones reagent (see Fieser and Fieser, *Reagents in Organic Synthesis*, Vol. 1, p. 242) at about $-10°$ to $10°$ C. in acetone to form an acetate-acid

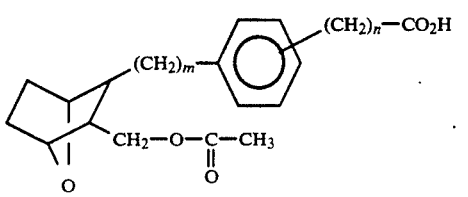

The acetate-acid V is reacted with an aqueous alkali metal hydroxide in tetrahydrofuran to form an alcohol-acid

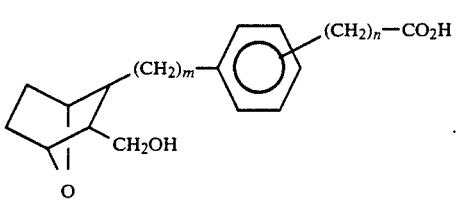

Alcohol-acid VI (or acetate-acid V) is then esterified with a solution of acid in alcohol (e.g., $HCl/CH_3OH$) at about $-10°$ to $10°$ C. to form an alcohol ester

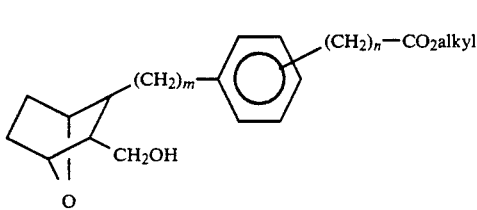

Alcohol-ester VII is oxided with Jones reagent at about $-10°$ to $10°$ C. in acetone to form an acid-ester

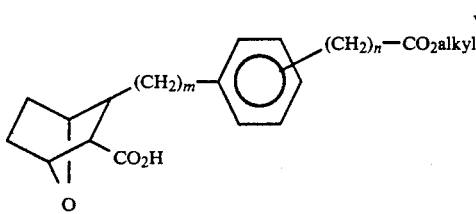

Acid-ester VIII reacts with hydrazine or hydrazine hydrochloride in an organic solvent (e.g., dimethylformamide) in the presence of a coupling reagent such as 1-(3-dimethylaminopropyl)-3-ethylcarbodiimide hydrochloride (WSC) or dicyclohexylcarbodiimide (DCC) and the catalyst hydroxybenzotriazole (HOBT) hydrate and an amine base (e.g., N-methylmorpholine) at about 20° to 30° C. under an inert atmosphere (e.g., argon) to form a hydrazide

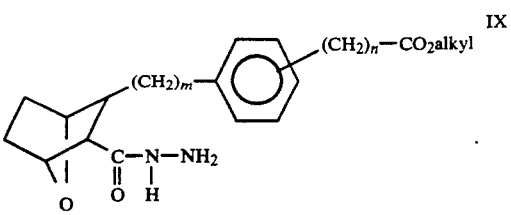

Hydrazide IX reacts with the thioamide

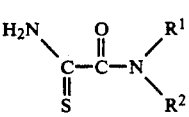 D in an organic solvent (e.g., methanol) under an inert atmosphere (e.g., argon) in the presence of sodium methoxide to form a thioamide

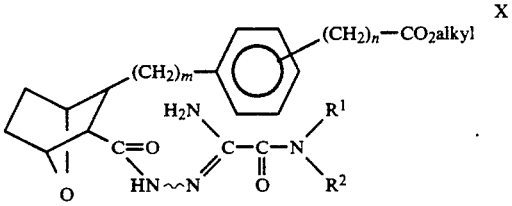

Thioamide D may be derived from 2,2-aminothioethanoic acid, ethyl ester, which is prepared as described in Boon, W. R., *J. Chem. Soc.* (1945), 601 and Oliver, J. E. and Sonnet, P. E. *J. Org. Chem.* 38 (1973), 1437. This ester is reacted with an amine reagent $HNR^1R^2$, (e.g., 4-cyclohexylbutylamine) to form thioamide D. Analogous preparations are described in Weddige, A., *J. Pract. Chem.*, 9 (1874), 132; Walter, W. and Bode, K. D., *Liebigs Ann. Chem.*, 660 (1962), 74.

Compound X undergoes cyclodehydration by heating to about 180° to 220° C. under high vacuum to form compound I wherein Y is a single bond, X is NH, R is $CO_2R'$ and $R'$ is alkyl. These thioamide coupling and cyclodehydration steps are analogous to procedures described in T. Vanek et al., *Coll. Czech. Chem. Comm.*, 49 (1984), 2492.

Alternatively, when X is O, compound VIII is converted to its acid chloride at about 0 to 30° C. under an inert atmosphere (e.g., argon) in an organic solvent (e.g., toluene) in the presence of oxalyl chloride and optionally in the presence of DMF. The acid chloride is then reacted with a hydroxyamide

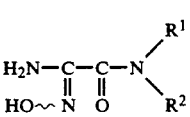 E in the presence of a base (e.g., pyridine) in an organic solvent (e.g., chloroform) under an inert atmosphere (e.g, argon) at about 0 to 30° C. to form

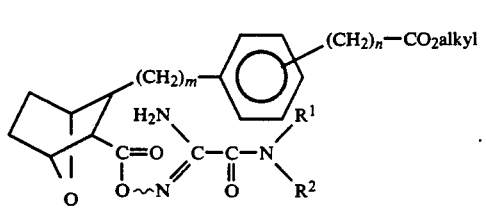

Compound XI undergoes cyclodehydration as described for compound X to form compound I wherein X is O, Y is a single bond, R is $CO_2R'$ and R' is alkyl. Analogous preparations are found in Hennen, W. J. and Robins, R. K., *J. Het. Chem.*, 22 (1985), 1747; European Patent Application 239, 309; and Ruccia, M. and Vivona, N., *Ann. Chim. (Rome)*, 58 (1968), 484. Hydroxyamide E is prepared by reacting thioamide D with hydroxyamine in methanol solution at about 20° to 30° C. under an inert atmosphere such as argon.

Compounds of the invention wherein Y is O may be prepared as follows.

Bromophenol $A^1$

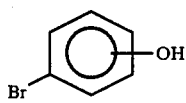

is treated with bromomethyl methyl ether to form the compound

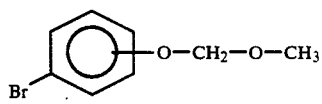

Compound $B^1$ is metallated (using a procedure similar to that set out above with respect to metal-halogen exchange of B using n-butyllithium in THF) and condensed with hemiacetal C to form the condensed 7-oxabicycloheptane compound

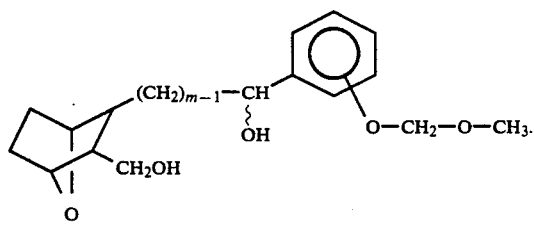

The condensed compound XII is then subjected to hydrogenolysis by treatment with hydrogen in the presence of a catalyst such as palladium on charcoal in acetic acid, to form the alcohol

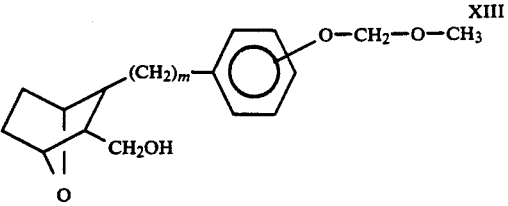

Compound XIII is deprotected by treatment with, for example, a solution of methanol and aqueous hydrochloric acid to form the deprotected alcohol

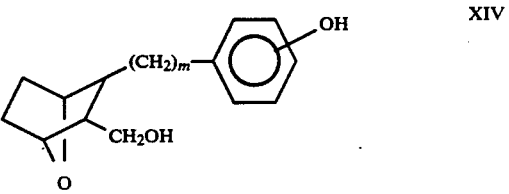

The alcohol XIV is then deprotonated by treating a solution of alcohol XIV in tetrahydrofuran with a molar equivalent of sodium hydride or one to four equivalents of a carbonate base such as potassium carbonate. The resulting phenoxide solution is alkylated by treating with a haloalkanoic acid ester

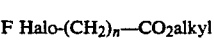

F   Halo-$(CH_2)_n$—$CO_2$alkyl employing a molar ratio of F:XIV of about 1:1 to 3:1 in the presence of an inert organic solvent (e.g., THF, dimethylformamide or dimethoxyethane) to form ester

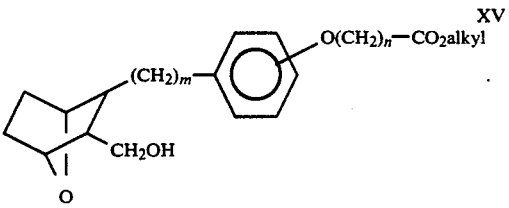

Alcohol ester XV is treated as described above for compound VII to form compound I wherein Y is —O—.

Compounds of formula I wherein Y is —CH═CH— may be prepared starting with alcohol A wherein n is 2, which may be prepared by subjecting the aldehyde

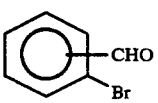

a Wittig reaction with $(C_6H_5)_3PCHCO_2CH_3$ to form ester

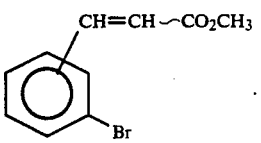

Ester H undergoes a double bond reduction by treatment with hydrogen in the presence of rhodium on alumina catalyst in the presence of methanol to form ester

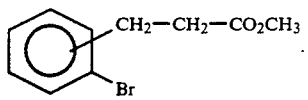

H¹

Ester H¹ is then reduced by treatment with diisobutylaluminum hydride in the presence of toluene solvent to form alcohol A wherein n is 2.

Alcohol A is used as described previously herein to form alcohol-ester VII wherein n is 2, which is treated with a silane protecting compound as described hereinbefore in the presence of an amine base (e.g., triethylamine) and an inert solvent (e.g., methylene chloride) and N,N-dimethylaminopyridine (DMAP) to form the protected alcohol

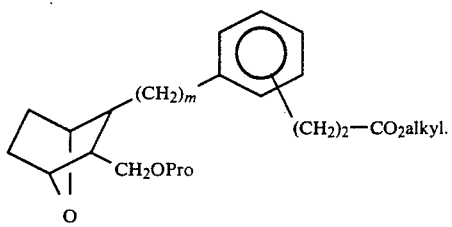

XVI

The protected alcohol XVI is then treated with lithium diisopropylamide in tetrahydrofuran solution at low temperature (−78° to 0° C.) under an inert atmosphere (e.g., argon). The resulting mixture is treated with diphenyl diselenide at about −78° to 25° C., to form the corresponding selenide

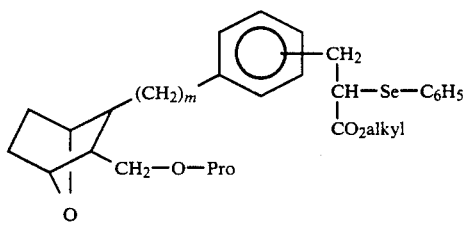

XVII

Selenide XVII in an inert organic solvent (e.g., ethyl acetate and/or methanol) is treated with an oxidizing agent (e.g., aqueous hydrogen peroxide) to form the cinnamate

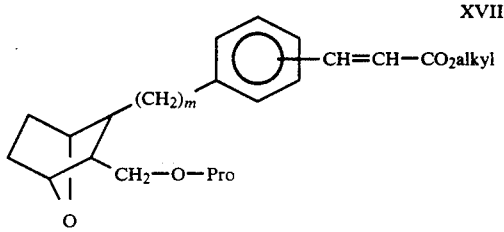

XVIII

The protecting group is removed from cinnamate XVIII by treatment with a solution of hydrogen chloride in methanol to form the alcohol

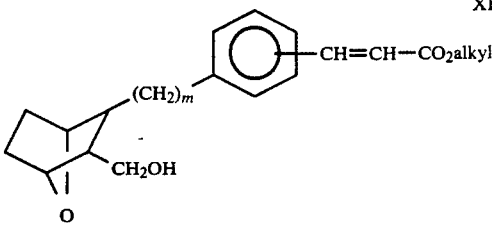

XIX which may then be employed to form compounds of formula I wherein Y is —CH=CH— employing procedures described for treatment of alcohol-ester VII.

The compounds of formula I wherein Z is —CH=CH— or —(CH₂)₂— may be prepared as follows.

Compounds of the invention where Z is —CH=CH— and preferably in the cis form, and X is O are prepared starting with the hydroxymethyl compound

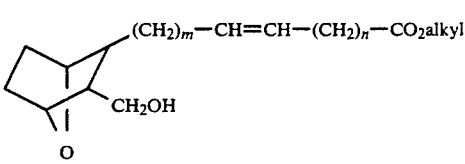

XX which is prepared as described in U.S. Pat. No. 4,143,054. Compound XX is subjected to a Jones oxidation with Jones' Reagent (CrO₃ dissolved or suspended in aqueous sulfuric acid, prepared as described in Fieser & Fieser, Reagents for Organic Synthesis, Vol I, p. 142 (1967)) in the presence of acetone under an inert atmosphere (e.g., argon) at about −10° to 20° C. to form the corresponding carboxylic acid-ester

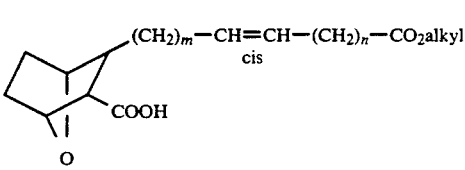

XXI

Acid-ester XXI is then reacted as described above for compounds VIII→IX→X→I (or VIII→XI→I) to form compound I wherein Z is —CH=CH—.

The trans double bond isomer wherein Z is —CH=CH— in formula I may be prepared starting with hydroxymethyl compound XX, which includes a cis double bond. Compound XX is treated with a protecting compound such as t-butyldimethylsilyl chloride or other silyl protecting group as described hereinbefore in the presence of imidazole or triethylamine and an inert organic solvent such as methylene chloride or tetrahydrofuran, to form the protected compound

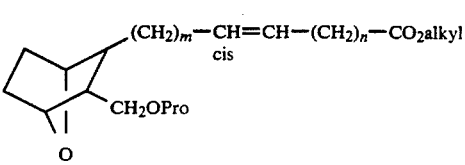

XXII

A solution of the protected alcohol in an inert organic solvent such as methylene chloride or acetone is treated with excess ozone at reduced temperature (about −78° to −60° C.) followed by treatment with dimethyl sulfide (molar ratio of XXII:(CH₃)₂S of about 0.01:1 to 0.2:1), to form the aldehyde

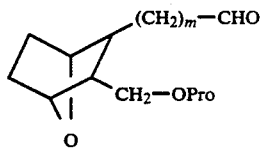
XXIII

Aldehyde XXIII is then treated with a mixture of lithium bromide or lithium chloride and trimethylphosphonoacetate and triethylamine in an inert organic solvent such as methylene chloride or chloroform to form the ester

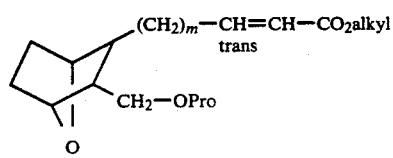
XXIV

A solution of ester XXIV in an inert organic solvent (e.g., tetrahydrofuran, diethyl ether or dimethyoxyethane) is cooled to about −78° to 0° C. and reacted with diisobutylaluminum hydride in an aromatic solvent such as toluene for about 0.5 to 4 hours to form alcohol

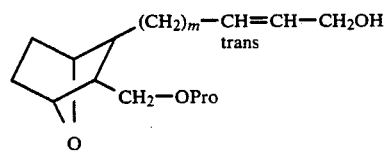
XXV

Alcohol XXV is treated with bromotriphenylphosphonium bromide (formed by adding bromine to triphenylphosphine in toluene or other aromatic solvent under argon at about −10° to 10° C.) in the presence of pyridine and toluene, at about −10° to 10° C. to form bromide

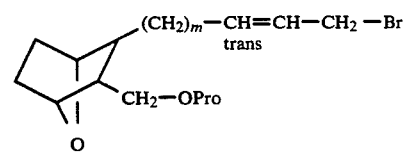
XXVI

An acetic acid ester such as t-butyl acetate or ethyl acetate is treated with a solution of LDA (lithium diisopropylamide) in an inert organic solvent such as tetrahydrofuran and at about −78° to −60° C. for about 0.5 to 2 hours, followed by addition of a solution of bromide XXVI in an inert solvent such as tetrahydrofuran to form ester

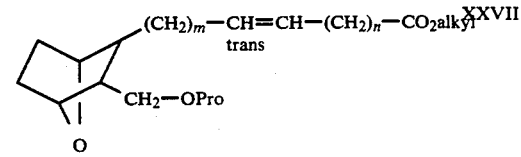
XXVII wherein n is 2.

For compounds of the invention wherein Z is —CH=CH— in the trans form and n is 1, 3, or 4, aldehyde XXIII is allowed to react with a phosphonium salt of formula

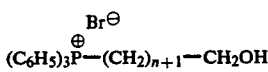
I in the presence of a strong base such as potassium t-amylate in toluene or NaH/dimethylsulfoxide to give

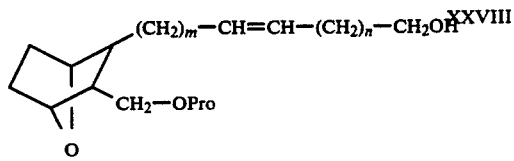
XXVIII which is oxidized and esterified using procedures known in the art to form ester XXVII wherein n is 1, 3 or 4.

Ester XXVII is then deprotected by treatment in methanol under an inert atmosphere such as argon with hydrochloric acid in methanol (prepared by adding acetyl chloride to methanol) to form alcohol

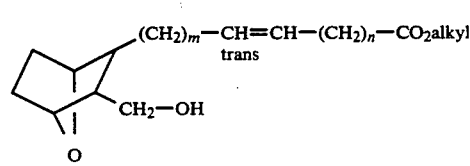
XXIX

Alcohol XXIX may then be used in place of compound XX as a starting material following the procedure hereinbefore described to form compound I wherein Z is —CH=CH— in the trans double bond isomeric form.

Compounds of formula I wherein Z is —(CH₂)₂— may be prepared from the corresponding acids wherein Z is —CH=CH— by hydrogenation using, for example, a hydrogenation catalyst (e.g., palladium on carbon) in an inert organic solvent (e.g., ethyl acetate or acetic acid).

Compounds of the invention wherein n is 0, Z is phenylene, and Y is a single bond may be prepared starting with a bromobenzyl alcohol

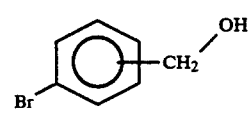
A² which is treated with a protecting compound (e.g., t-butylchlorodiphenylsilane) in the presence of 4-dimethylaminopyridine and an amine base (e.g., triethylamine) in an inert solvent (e.g., methylene chloride) to form the protected bromobenzyl compound

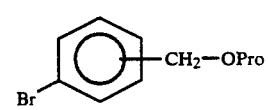
B² wherein Pro represents a protecting group.

Examples of protecting compounds suitable for use herein are as set out hereinbefore in reacting with bromophenalkyl alcohol A, with the exclusion of benzyl bromide.

The protected compound B² is metallated by treatment with t-C₄H₉Li or n-C₄H₉Li in the presence of diethyl ether or THF at about −100° to 0° C. or is subjected to a Grignard reaction by treatment with magnesium in the presence of an inert organic solvent such as THF or diethyl ether. The so-treated compound B² is then condensed with compound C in a C:B² molar ratio of about 1:2 to 1:4 in the presence of an inert organic solvent such as THF at about −78° to 25° C. to form a condensed 7-oxabicycloheptane compound

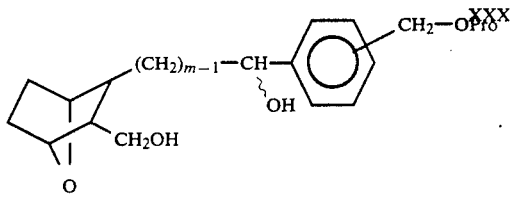

Compound XXX is then protected by treatment with, for example, a solution of acetic anhydride and pyridine in the presence of 4-dimethylaminopyridine to form compound

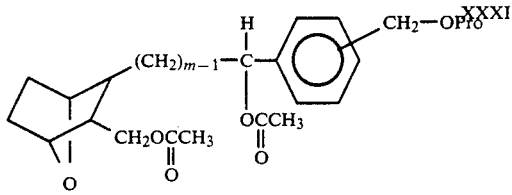

The protected alcohol XXXI is then deprotected using conventional procedures, and the resulting alcohol is subjected to a Jones oxidation employing procedures described hereinbefore to form a crude acid. The crude acid is deacetylated by reaction with aqueous hydroxide in the presence of an inert organic solvent such as THF and then esterified, for example, by treatment with a diazoalkane (e.g., diazomethane) or acidic alcohol, to form the alcohol ester

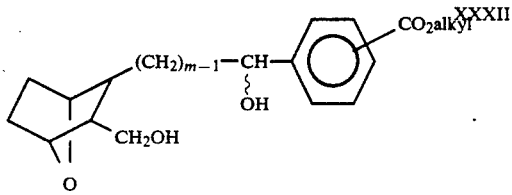

The alcohol ester XXXII is then subjected to hydrogenolysis as described above to provide the alcohol ester

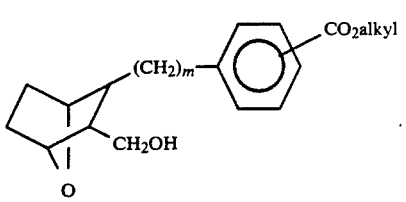

Next, the alcohol ester XXXIII is subjected to a Jones oxidation to form the acid ester

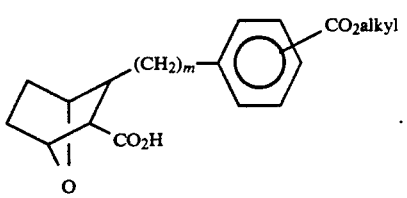

Acid ester XXXIV is treated as described above for compound VIII to form compound I wherein Z is phenylene, Y is a single bond, and n is 0.

Compounds of formula I wherein R is CO₂R' and R' is alkali metal can be prepared from the corresponding esters by treating the ester with bases such as lithium hydroxide or potassium hydroxide. The corresponding acids (wherein R' is hydrogen) are prepared by neutralizing the foregoing alkali metal salts with an acid (e.g., dilute hydrochloric acid or oxalic acid).

Compounds of formula I wherein R is —CH₂OH may be prepared by treating the corresponding esters (wherein R is CO₂R' and R' is alkyl) with a reducing agent such as LiBH₄ in the presence of diethyl ether and THF.

Compounds of the invention wherein R is CONH-SO₂R³ are prepared by treating the associated acids (wherein R is CO₂H) with a sulfonamide

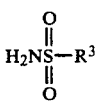

in the presence of a coupling agent (e.g., dicyclohexylcarbonyldiimide or WSC) in the presence of dimethylaminopyridine under an inert atmosphere (e.g., argon).

Compounds wherein R is —CH₂-5-tetrazolyl are prepared by reacting the associated ester with, in sequence, (1) a hydride reducing reagent (e.g., lithium borohydride or sodium borohydride), (2) triphenylphosphonium dibromide in an inert solvent such as toluene, (3) an alkali metal cyanide in a polar solvent such as methanol/water, and (4) sodium azide in the presence of ammonium chloride, DMF and lithium chloride at about 100 to 130° C.

Compounds of formula I wherein R is CONHR⁴ wherein R⁴ is other than hydrogen may be prepared from the corresponding acid by treatment with WSC in the presence of DMF, HOBT, an organic base (e.g., triethylamine) and an amine

K

HNHR⁴.

Where $R^4$ is hydrogen, ammonium chloride is used in place of the above amine.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared with starting materials and procedures in U.S. Pat. No. 4,143,054.

The nucleus in each of the compounds of the invention is depicted as

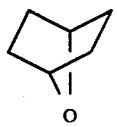

for convenience; the nucleus may also be depicted as

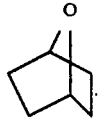

Use and Utility

The compounds of this invention are thromboxane receptor antagonists and as such are useful as inhibitors of thromboxane receptor mediated actions. The term "thromboxane receptor antagonist" includes compounds that are so-called thromboxane $A_2$ receptor antagonists, thromboxane $A_2$ antagonists, thromboxane $A_2$/prostaglandin endoperoxide antagonists, TP-receptor antagonists, or thromboxane antagonists.

The compounds of the invention are also thromboxane synthetase inhibitors and thus are useful as inhibitors of thromboxane production.

The compounds of this invention are useful as inhibitors of platelet function, i.e., for the prevention and treatment of thrombotic vascular occlusive disorders, whether complete or partial, for example, arterial thrombosis, including that of the coronary, cerebral, ophthalmic, hepatic, mesenteric, renal, peripheral arteries or vascular or organ grafts, unstable angina, transient ischemic attacks, or intermittent claudication. They may be useful to prevent thrombosis following vascular injury produced in the course of diagnostic or therapeutic procedures such as endarterectomy or angiography. The compounds may be useful in the treatment or prevention of disorders characterized by platelet consumption and/or activation, including, platelet activation, dysfunction, and/or loss during extracorporeal circulation, the use of radiographic contrast agents, thrombotic thrombocytopenia purpura, disseminated intravascular coagulation, purpura fulminans, hemolytic transfusion reaction, or hemolytic uremic syndrome, systemic lupus, cyclosporine-induced renal toxicity, pulmonary hypertension, side effects from dialysis, or abdominal aortic aneurism repair. The compounds may be used in the treatment of venous thrombosis or embolism, including pulmonary embolism, deep venous thrombosis, hepatic vein thrombosis, and renal vein thrombosis.

The compounds of this invention are useful as inhibitors of arterial or venous vasoconstriction. Accordingly, they may be useful to prevent vasoconstriction associated with unstable angina, chronic stable angina, and variant, or Prinzmetal's angina, Raynaud's syndrome, migraine headache, vasospasm of the coronary, cerebral, ophthalmic, hepatic, mesenteric, renal, peripheral arteries or vascular grafts, vascular injury such as that associated with surgery or trauma. Hypertension of pregnancy, the hepato-renal syndrome, and pulmonary hypertension are additional examples of vasoconstrictive disorders treatable by the compounds of this invention.

The compounds of this invention are useful as inhibitors of bronchoconstriction, i.e., airway hyperresponsiveness, allergic bronchospasm, asthma, and bronchoconstrictive responses to environmental, infectious, noxious or mechanical stimuli.

The compounds of this invention are useful as inhibitors of ischemic and reperfusion injury to various tissues, including, myocardium, skin, brain, bowel, or kidney, alone or in combination with other agents intended to restore blood flow. For example, these compounds may be useful for improving postischemic myocardial function and decreasing myocardial infarct size. Ischemia caused by reduced blood flow during diagnostic or therapeutic procedures may benefit by treatment with these compounds, for example, they reduce the myocardial stunning observed after bypass surgery. In addition, they may be useful for reducing the tissue injury caused by a stroke.

The compounds of this invention may be useful in the prevention or treatment of other conditions including burns, diabetic retinopathy, tumor metastases and tardive dyskinesia. The compounds may be useful in potentiating diuretic-induced diuresis.

In addition, the thromboxane receptor antagonists of the invention may be used with a thrombolytic agent such as t-PA, streptokinase, urokinase, prourokinase or anisoylated plasminogenstreptokinase activator complex (APSAC) within 6 hours of a myocardial infarction. In such case, the thrombolytic agent may be used in amounts conventionally employed, for example, as disclosed in the Physicians' Desk Reference for reducing post-ischemic myocardial injury.

The compounds of the invention can be administered orally or parenterally to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The active substance can be utilized in a composition such as tablet, capsule, solution or suspension containing about 5 to about 500 mg per unit of dosage of a compound or mixture of compounds of formula I or in topical form for wound healing (0.01 to 5% by weight compound of formula I, 1 to 5 treatments per day). They may be compounded in conventional matter with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice. Also as indicated in the discussion above, certain members additionally serve as intermediates for other members of the group.

The compounds of the invention may also be administered topically to treat peripheral vascular diseases and as such may be formulated as a cream or ointment.

Preferred Embodiments

The following Examples represent preferred embodiments of the present invention. Unless otherwise indicated, all temperatures are expressed in degrees Celsius.

EXAMPLE 1

1S-(1α,2α,3α,4α)]-2-[[3-[3-[[(4-Cyclohexylbutyl)amino]carbonyl]-1,2,4-oxadiazol-5-yl]-7-oxabicyclo[2.2.1]hept-2-yl]methyl]benzenepropanoic acid, methyl ester

A. 3-(2-Bromophenyl)-2-propenoic acid, methyl ester

To a stirred solution of 161.2 g (871 mmol) of 2-bromobenzaldehyde in 700 mL of dry THF (distilled from potassium/benzophenone) at room temperature under argon, was added 298.4 g (892 mmol, 1.024 equiv) of methyl(triphenylphosphoranylidene)acetate (Aldrich) over 1 hour in 20 g portions. Reaction was mildly exothermic and the mixture became homogeneous. The resulting solution was stirred for 18 hours during which some precipitate formed. Addition of 200 mL hexane caused further precipitation. Filtration was followed by evaporation. The residue was slurried with a large volume of hexane (more precipitation) and refrigerated overnight. This was filtered, and the filtrate was passed through a plug of silica gel (approximately 1 kg), eluting with 10% ethyl acetate (EtOAc) in hexane. The eluant was concentrated in vacuo to give 201.5 g of a colorless oil. This oil was pure title compound as a 4:1 mixture of double bond isomers (trans predominating). The yield of title compound was 96%.

B. 2-Bromobenzenepropanoic acid, methyl ester

A mixture of 201.5 g (836 mmol) of the Part A acrylate and 8.4 g of 5% rhodium on alumina catalyst (MCB) in 1.0 L of methanol was stirred at room temperature under an atmosphere of hydrogen (balloon) for over 8 hours. $^1$H NMR analysis of an aliquot showed about a 1:1 mixture of title compound and trans Part A compound with no cis Part A compound. The mixture was diluted with 500 mL additional methanol (MeOH) and 12.6 g more catalyst was added. After hydrogenation overnight, the reaction was complete. The reaction mixture was passed through Celite and a Millipore/Fluropore membrane filter (0.5 μm FH) with a prefilter pad, and the filtrate was concentrated in vacuo to obtain two immiscible oils. One of the oils was water-soluble and gave a highly acid aqueous solution. Solid NaHCO₃ and Na₂SO₄ were carefully added (gas was evolved). The mixture was diluted with CH₂Cl₂, filtered, and evaporated (and re-evaporated with CH₂Cl₂ to drive off methanol) to obtain 196.9 g of clear oil. This oil was 95% pure title compound with 5% of dibromo title compound. The corrected yield of the title compound was 92% (187.1 g).

C. 2-Bromobenzenepropanol

To a stirring solution of 196.9 g (95% pure=187.1 g, 770 mmol) of compound B in 770 mL of toluene under argon cooled to 0° C. (ice bath), 830 mL of 1.0M diisobutylaluminum hydride (DIBAL-H) in toluene solution (830 mmol, Aldrich) was added over 45 minutes. The reaction was not very exothermic. After the mixture was stirred for 1 hour, TLC indicated approximately half of the starting material remained. Next, 580 mL of 1.5M DIBAL-H in toluene solution (870 mmol, Aldrich) was added slowly. The ice bath was removed and stirring was continued for 2 hours. The mixture was then poured slowly into 1.2 L of 6M aqueous HCl stirring in an ice bath. This quench was exothermic and gas was evolved. After the mixture was recooled to 0°, the layers were separated, and the organic layer was washed with 1M aqueous HCl and brine. It was then dried over Na₂SO₄ and MgSO₄ and evaporated (and re-evaporated with CH₂Cl₂ to drive off toluene) to obtain 173.0 g of clear, colorless oil. This oil was 95% pure title compound with 5% of dibromo title compound. The corrected yield of the title compound was 99% (164.3 g).

D. 1-Bromo-2-[3-[[Dimethyl(1,1,2-trimethylpropyl)silyl]oxy]propyl]benzene

To a solution of 29.0 g (135 mmol) of the crude Part C alcohol and 24.1 g (135 mmol, Petrarch) of thexyldimethylchlorosilane in 200 mL of dry methylene chloride (distilled from phosphorous pentoxide) was added at room temperature 20 mL (143 mmol, distilled from calcium hydride) of triethylamine and then 200 mg (1.64 mmol, Aldrich) of 4-dimethylaminopyridine. The reaction mixture was stirred at room temperature for 18 hours. The resulting slurry was diluted with 100 mL of hexane, cooled to 0° C. with stirring for 15 minutes, then filtered to remove solid triethylamine hydrochloride. The filtrate was concentrated in vacuo to give an oil. The crude oil was purified by flash chromatography (Merck silica, 15×10 cm, 1:9 ethyl acetate/petroleum ether) to afford 45.5 g (127 mmol, 94%) of the title compound as a colorless liquid.

E. [1S-(1α,2α,3α,4α)]-[2-[3-[[Dimethyl(1,1,2-trimethylpropyl)silyl]oxy]propyl]phenyl]-7-oxabicyclo[2.2.1]heptane-2,3-dimethanol To a solution of 5.00 g (14.0 mmol) of compound D in 30 mL of dry diethyl ether (distilled from ketyl) cooled to −100° C. was added dropwise 15 mL (1.7M in pentane, 25 mmol, Aldrich) of t-butyllithium solution over 15 minutes. The reaction mixture was stirred at −100° C. for 15 minutes then at 0° C. for 15 minutes. The resulting pale yellow anion solution was recooled to −78° C., 30 mL of dry THF (distilled from ketyl) was introduced, and a solution of 875 mg (5.61 mmol) of [3aR-(3aα,4β,7β)]-octahydro-4,7-epoxyisobenzofuran-(1-ol in 10 mL of THF was rapidly added. The reaction mixture was warmed to 0° C., stirred for 1 hour, quenched with 5 mL of water, then partitioned between 100 mL of water and 25 mL of ethyl acetate. The organic layer was separated and the aqueous layer was extracted with an additional 25 mL of ethyl acetate. The organic extracts were combined, dried (magnesium sulfate), and concentrated in vacuo to give an oil. The crude oil was purified by flash chromatography (Merck silica, 12×5.0 cm, 1:4 ethyl acetate/petroleum ether then 4:1 ethyl acetate/petroleum ether) to afford 2.35 g (5.41 mmol, 97%) of the title diasteromeric alcohols as a colorless oil.

F.
[1S-(1α,2α,3α,4α)]-2-[[2-[3-[[Dimethyl(1,1,2-trimethylpropyl)silyl]oxy]propyl]phenyl]methyl]-7-oxabicyclo[2.2.1]heptane-3-methanol A mixture of 1.90 g (4.38 mmol) of the Part E diastereomeric alcohols and 1.9 g of 20% palladium hydroxide on carbon catalyst (moist, less than 50% water, Aldrich) in 60 mL of glacial acetic acid was stirred rapidly under an atmosphere of hydrogen (balloon) for 5 hours. The reaction mixture was filtered through a 4 μM polycarbonate membrane and the filtrate was concentrated in vacuo (room temperature bath). The residue was partitioned between 50 mL of water and 50 mL of ethyl acetate. The organic layer was separated, washed with 50 mL of 1M aqueous sodium hydroxide solution, dried (magnesium sulfate), and concentrated in vacuo to give an oil. The crude material was purified by flash chromatography (Merck silica, 12×5.0 cm, 1:2 ethyl acetate/petroleum ether) to afford 1.03 g (2.39 mmol, 55%) of the title compound as a colorless oil. In addition, 573 mg (1.37 mmol, 30%) of the Part E starting material (as a single diastereomer) was recovered.

G.
[1S-(1α,2α,3α,4α)]-2-[[3-(Hydroxymethyl)-7-oxabicyclo[2.2.1]hept-2-yl]methyl]benzenepropanoic acid, methyl ester A solution of 1.00 g (2.39 mmol) of compound F and 50 mg (0.41 mmol, Aldrich) of 4-dimethylaminopyridine in 6 mL of 1:1 dry pyridine/acetic anhydride was stirred at room temperature for 2 hours. The reaction mixture was concentrated in vacuo and the residue partitioned between 25 mL of ethyl acetate and 20 mL of 1M aqueous HCl solution. The organic layer was separated, washed with 20 mL of 1M aqueous NaOH and 20 mL of brine, dried (magnesium sulfate), and concentrated in vacuo to afford the crude acetate as an oil.

To a solution of the crude acetate in 15 mL of reagent acetone cooled to 0° was added rapidly 3.3 mL of Jones reagent (2.6M in $Cr^{+6}$, see Fieser & Fieser, *Reagents for Organic Synthesis*, Vol. 1, p. 142). The reaction mixture was stirred for 2 hours, quenched by addition of 1 mL of isopropanol and stirred for an additional 30 minutes. The resulting green slurry was filtered through a pad of Celite. The filtrate was concentrated in vacuo and the residue partitioned between 25 mL of diethyl ether and 25 mL of water. The organic layer was separated and concentrated in vacuo to give the crude acetate-acid as an oil.

A solution of the crude acetate-acid in 15 mL of 2:1 1M aqueous NaOH/THF was stirred at room temperature for 30 minutes. The reaction mixture was cooled in an ice-bath, quenched by 15 mL of 1M aqueous HCl solution, then extracted with two 25-mL portions of diethyl ether. The ether extracts were combined, washed with 25 mL of brine and concentrated in vacuo to give the crude alcohol-acid as an oil.

A solution of the crude alcohol-acid in 10 mL of acidic methanol (prepared by addition of 0.5 mL of acetyl chloride to 10 mL of dry methanol at 0° C.) was stirred at 0° for 2 hours and then concentrated in vacuo. The resulting oil was purified by flash chromatography (Merck silica, 15×3.0 cm, ethyl acetate) to afford 526 mg (1.76 mmol, 74% from compound F) of the title compound as a colorless oil.

H.
[1S-(1α,2α,3α,4α)]-2-[[3-Carboxy-7-oxabicyclo[2.2.1]hept-2-yl]methyl]benzenepropanoic acid, methyl ester To a solution of 495 mg (1.63 mmol) of compound G in 5 mL of reagent acetone cooled to 0° C. was added rapidly 2.0 mL (2.6M in $Cr^{+6}$) of Jones reagent. The reaction mixture was warmed to room temperature, stirred for 2 hours, then quenched by about 1 mL of isopropanol. After 15 minutes, the resulting green slurry was filtered through a pad of Celite. The filtrate was partitioned between 20 mL of diethyl ether and 20 mL of water. The organic layer was separated, and the aqueous layer was extracted with an additional 20 mL of diethyl ether. The ether extracts were combined, dried (magnesium sulfate), and concentrated in vacuo to give 560 mg (1.59 mmol, 98%) of crude title compound as a colorless oil.

I.
2,2-Aminothio-1-[(4-cyclohexylbutyl)amino]-1-ethanone 2,2-Aminothioethanoic acid, ethyl ester was prepared as described in Boon, W. R., *J. Chem. Soc.* (1945), 601 (see also Oliver, J. E. and Sonnet, P E., *J. Org. Chem.* 38 (1973), 1437 note 6). A solution of pure 2,2-aminothioethanoic acid, ethyl ester (7.06 g, 53.1 mmol) in 10 mL of methanol was stirred at room temperature under argon as 7.35 g of 4-cyclohexylbutylamine (47.4 mmol) was added. A mildly exothermic reaction ensued, during which the reaction mixture warmed significantly. After about 30 minutes, a precipitate began to form. TLC indicated that both starting materials had been consumed completely and several products had formed. The precipitate was filtered. It was not the desired title compound ($H_2NCSCONHR$), but rather RNHCSCONHR. The mother liquors were evaporated, and flash chromatography (10% to 100% EtOAc in hexane gradient, discarding mixed fractions) was used to isolate four other products. Aside from 2.24 g of the title compound ($H_2NCSCONHR$), the regioisomer RNHCSCONH$_2$, and two other compounds, $H_2NCSCONH_2$ and either $H_3COCSCONHR$ or RNHCSCOOCH$_3$ were isolated. The yield of the title compound, a yellow solid, was 20%.

For analogous preparations, see a) A. Weddige, *J. Pract. Chem.* 9 (1874), 132. b) W. Walter and K.-D. Bode, *Liebigs Ann. Chem.*, 660 (1962), 74. For spectroscopic data of related compounds, see R. A. Dommisse, et al., *Bull. Soc. Chim. Belg.*, 88 (1979), 261.

| TLC: (25% EtOAc in hexane - anisaldehyde): | |
|---|---|
| 2,2-aminothioethanoic acid, ethyl ester | 0.29 |
| 4-cyclohexylbutylamine | 0.00 |
| title compound | 0.40 |
| RNHCSCONHR | 0.71 |
| RNHCSCONH$_2$ | 0.33 |
| H$_2$NCSCONH$_2$ | 0.10 |
| H$_3$COCSCONHR or RNHCSCOOCH$_3$ | 0.50 |
| $^{13}$C NMR (67.8 MHz in CDCl$_3$): | |
| 191.3, 158.0, 40.8, 37.4, 36.9, 33.3, 29.3, 26.6, 26.3, 24.1 | |

J.
2-Amino-2-hydroxyimino-1-[(4-cyclohexylbutyl)amino]-1-ethanone 14.1 mL of 25% sodium methoxide in methanol solution (4.37M, 61.7 mmol) was added to a solution of 4.29 g of H$_{NOH}$.HCl (61.7 mmol) in 50 mL of methanol. The neutralization was mildly exothermic, and the mixture was allowed to cool to room temperature and fully precipitate NaCl. The supernatant (approximately 1M methanolic hydroxylamine solution) was then drawn.

A solution of 0.69 g of pure part I compound (2.85 mmol) in 10 mL of methanol was stirred at room temperature under argon as 6 mL of the approximately 1M methanolic solution of hydroxylamine (6 mmol) was added. After stirring for 5 hours, the mixture was diluted with CH$_2$Cl$_2$ and water was added. The mixture was extracted three times with CH$_2$Cl$_2$, the extracts were dried over Na$_2$SO$_4$, and evaporation gave 0.71 g (quantitative yield) of pure title compound as a white solid.

TLC (25% ethyl acetate in hexane-anisaldehyde):
Compound I 0.36
Compound J 0.14

K.
[1S-(1α,2α,3α,4α)]-2-[[3-[[[[1-Amino-2[(4-cyclohexylbutyl)amino]-2-oxoethylidene]amino]oxy]carbonyl]-7-oxabicyclo[2.2.1]hept-2-yl]methyl]benzenepropanoic acid, methyl ester A solution of 0.75 g of pure compound H (2.36 mmol) in 15 mL of toluene was stirred at room temperature under argon as 0.26 mL of oxalyl chloride (0.38 g, 3.0 mmol) was added. The mixture bubbled. After 5 minutes, a small drop (about 3 mg) of dimethylformamide was added, and the bubbling accelerated. After about 1 hour the bubbling had stopped and the solvent was evaporated. The resulting acid chloride was dissolved in 4 mL of CHCl$_3$ and transferred (using two additional 4 mL portions of CHCl$_3$ to transfer residual acid chloride) to a solution of 0.68 g of pure amidoxime compound J (2.8 mmol, 1.2 equiv) and 0.4 mL of pyridine (0.4 g, 5 mmol, 2 equiv) in 25 mL of CHCl$_2$, stirring at room temperature under argon. After stirring overnight (reaction was complete much sooner), the mixture was evaporated. Flash chromatography (30% to 50% EtOAc in hexane gradient) gave 1.21 g of pure compound K as a white solid. The yield of compound K was 95%.

For analogous preparations, see a) W. J. Hennen and R. K. Robins, *J. Het. Chem.*, 22, (1985), 1747. b) European Patent 0239309 c) M. Ruccia and N. Vivona, *Ann. Chim.* (Rome), 58, (1968) 484.

TLC (50% (5% AcOH in EtOAc) in hexane-anisaldehyde):
Compound J 0.63
Compound H 0.39
Compound K 0.44

$^{13}$C NMR (67.8MHz in CDCl$_3$): 173.3, 168.6, 158.7, 148.7, 138.5, 137.9, 130.1, 128.9, 126.7, 126.5, 78.6, 77.7, 51.6, 49.0, 39.7, 37.4, 36.9, 34.7, 33.2, 32.4, 29.5, 28.7, 27.4, 26.6, 26.3, 24.0

L.
[1S-(1α,2α,3α,4α)]-2-[3-[3-[[(4-Cyclohexylbutyl)amino]carbonyl]-1,2,4-oxadiazol-5-yl]-7-oxabicyclo[2.2.1]hept-2-yl]methylbenzenepropanoic acid, methyl ester 0.73 g of pure compound K (1.35 mmol) was placed under high vacuum (4 torr) and heated to 200° C. (The material melted and began to bubble at about 185°.) After 1.5 hours, TLC indicated nearly complete conversion to compound L with a small amount of compound J present. The material was cooled, and flash chromatography (25% to 40% EtOAc in hexane gradient) gave 0.64 g of pure compound L as a white solid. The yield of compound L (Example 1) was 90%.

TLC (50% EtOAc in hexane-anisaldehyde):
Compound L 0.40
Compound K 0.32
Compound J 0.06 (streaks)

$^{13}$C NMR (67.8MHz in CDCl$_3$): 180.1, 173.0, 163.3, 156.1, 138.5, 137.1, 129.6, 128.9, 126.8, 126.5, 79.6, 78.5, 51.5, 49.6, 45.7, 39.7, 37.4, 36.9, 34.8, 33.2, 32.2, 29.8, 29.5, 28.7, 27.5, 26.6, 26.3, 24.1.

EXAMPLE 2

[1S-(1α,2α,3α,4α)]-2-[[3-[3-[[(4-Cyclohexylbutyl)amino]carbonyl]-1,2,4-oxadiazol-5-yl]-7-oxabicyclo[2.2.1]hept-2-yl]methyl]benzenepropanoic acid
AND

EXAMPLE 3

[1S-(1α,2α,3β,4α)]-2-[[3-[3-[[(4-Cyclohexylbutyl)amino]carbonyl]-1,2,4-oxadiazol-5-yl-7-oxabicyclo[2.2.1]hept-2-yl]methyl]benzenepropanoic acid A solution of 340 mg of nearly pure Example 1 (95% pure=323 mg, 0.62 mmol) in 10 mL of THF, 4 mL of 1.0M aqueous NaOH, and 10 mL of methanol was prepared and stirred at room temperature under argon. After 30 minutes, TLC (using both 50% EtOAc in hexane and the TLC solvent system below) showed that all Example 1 had been consumed and two carboxylic acid products had formed. Furthermore, a trace of another compound, presumably Example 3 methyl ester, which subsequently disappeared, was present. After 50 minutes addition of CH$_2$Cl$_2$, water, and brine was followed by acidification to pH 1 with 1.0M aqueous hydrochloric acid. The mixture was extracted three times with CH$_2$Cl$_2$. The combined extracts were dried over Na$_2$SO$_4$ and evaporated. Flash chromatography (silica gel, 25% to 60% (5% acetic acid in EtOAc) in hexane), followed by coevaporation with CH$_2$Cl$_2$ and toluene gave 41 mg of pure Example 2 as an oil, yield 13%. [α]$_D$= +5.95° in CHCl$_3$ at c=2.05 g/100 mL. Also isolated was about 300 mg (the balance of the mass) of Example 3 as an oil.

[α]$_D$= +48.7° in CHCl$_3$ at C=1.68 g/100 mL TLC (50% 5% acetic acid (AcOH) in EtOAc in hexane-anisaldehyde):

| Example 1 | 0.42 |
| Example 2 | 0.26 |
| Example 3 | 0.42 |

[1S-(1α,2α,3α,4α)]-2-[3-[5-[[(4-Cyclohexylbutyl)amino]carbonyl]-1H-1,2,4-triazol-3-yl]-7-oxabicyclo[2.2.1hept-2-yl]methylbenzenepropanoic acid, methyl ester

A.
[1S-(1α,2α,3α,4α]-2-[[3-(Hydrazinocarbonyl)amino]carbonyl]-1H-1,2,4-triazol-3-yl]-7-oxabicyclo[2.2.1-hept-2-yl]methyl]benzenepropanoic acid, methyl ester To a solution of 1.3 g of pure compound H from Example 1 (4.1 mmol) in 14 mL of N,N-dimethylformamide stirring at room temperature under argon, was added 0.56 g of HOBT hydrate (4.1 mmol, 1.0 equiv), 2.0 mL of N-methylmorpholine (1.8 g, 18 mmol, 4.4 equiv), 0.35 of N$_2$H$_4$ HCl (5.1 mmol, 1.2 equiv), and lastly 0.86 g WSC (4.5 mmol, 1.1 equiv.). After 3 hours, 80 mg of N₂H₄ (free base, mmol) and 0.10 g additional WSC were added to drive the reaction to completion. After 2.5 hours, the mixture was coevaporated three times with toluene to remove N,N-dimethylformamide. Flash chromatography silica gel, 5% (10% concentrated aqueous NH₃ in methanol) methylene chloride, discarding mixed fractions] allowed isolation of mg of hydrazide A, a white solid.

TLC (10% (10% concentrated aqueous NH₃ in methanol) in CH₂Cl₂—anisaldehyde):

Compound H, Example 1 0.09 (streaks)
Compound A, Example 4 0.38

¹³C NMR (67 8MHz in CDCl₃): 173.0, 172 2, 138.5, 138.0, 129.5, 128.8, 126.4, 126.4, 78.8, 78.4, 53.5, 51.5, 47.9, 34.8, 31.8, 29.4, 28.7, 27.4

B.
[1S-(1α,2α,3α,4α)]-2-[[3-[[2-[1-Amino-2-[(4-cyclohexylbutyl)amino]-2-oxoethylidene]hydrazino]carbonyl]-7-oxabicyclo[2.2.21]hept-2-yl]methylbenzenepropanoic acid, methyl ester To a solution of 0.31 g of hydrazide A (0.93 mmol) and 0.29 g of thioamide I from Example 1 (1.2 mmol, 1.3 equiv) in 20 mL of methanol stirring at room temperature under argon, was added 2.0 mL of 25% sodium methoxide in methanol solution (4.37M, 8.7 mmol, 9.4 equiv). After stirring overnight, the mixture was diluted with CH₂Cl₂, and water and brine were added. The mixture was extracted three times with CH₂Cl₂, the extracts were dried over Na₂SO₄, and the solvent was evaporated. Flash chromatography [silica gel, 2% to 5% (10% concentrated aqueous NH₃ in methanol) in methylene chloride gradient] gave 417 mg of pure compound B as a gum, yield 83%. ¹H NMR showed what appeared to be two isomers (4:1).

For an analogous preparation, see T. Vanek, et al., *Coll. Czech., Chem. Comm.*, 49 (1984), 2492.

TLC (10% [10% concentrated aqueous NH₃ in methanol]in CH₂Cl₂—anisaldehyde):
Compound A, Example 4 0.35
Compound I, Example 1 0.71
Compound B, Example 4 0.39

[1S-(1α,2α,3α,4α)]-2-[3-[5-[(4-Cyclohexylbutyl)amino]-carbonyl]-1H-1,2,4-triazol-3-yl]-7-oxabicyclo[2.2.1-]hept-2-yl]methyl]benzenepropanoic acid, methyl ester 100 mg of pure compound B (0.19 mmol) was placed under high vacuum (4 torr) and heated to 200° C. (As the temperature was increased, the gum first solidified and then melted at about 185° C.) After 1 hour, ¹H-NMR indicated a ratio of B to C of about 4:1. Continued heating under vacuum for 7 hours more drove the reaction essentially to completion. The material was cooled, and flash chromatography (4% 2-propanol in toluene, discarding mixed fractions) gave about 60 mg of nearly pure compound C as a white solid, 60%.

TLC (6% 2-propanol in toluene-anisaldehyde):

| | |
|---|---|
| B | 0.16 |
| C | 0.23 |

¹³C NMR (67.8MHz in CDCl₃) 173.4, 158.7, 138.5, 138.3, 129.7, 128.9, 126.4, 126.4, 80,7, 78.8, 51.6, 49.6, 46.2, 39.5, 37.5, 37.1, 35.0, 33.3, 32.7, 29.8, 29.6, 29.3, 27.7, 26.6, 26.3, 24.2

EXAMPLE 5

[1S-(1α,2α,3α,4α)]-2-[[3-[5-[[(4-Cyclohexylbutyl)amino]carbonyl]-1H-1,2,4-triazol-3-yl]-7-oxabicyclo[2.2.1]hept-2-yl]methyl]benzenepropanoic acid A solution of about 60 mg of nearly pure Example 4 (about 0.11 mmol) in 5 mL of tetrahydrofuran and 10 mL of methanol was prepared under argon with gentle warming and then cooled to room temperature. To this was added 4 mL of 1.0M aqueous NaOH solution. After 3 hours, the addition of CH₂Cl₂ and brine was followed by acidification to pH 1 with 1.0M aqueous hydrochloric acid. The mixture was extracted three times with CH₂Cl₂. The combined extracts were dried over Na₂SO₄ and evaporated. Flash chromatography [silica gel, 10% (50% AcOH in 2-propanol) in toluene], followed by coevaporation with CH₂Cl₂ and toluene gave 49 mg of Example 5 as a white solid (melting point 210° to 213° C., yield about 80%).

$[\alpha]_D = +8.09°$ in 50% methanol in CHCl₃ at c=1.31g/100 mL.

TLC (4% AcOH in (6% 2-propanol in toluene)-anisaldehyde):

| | |
|---|---|
| Example 4 | 0.23 |
| Example 5 | 0.15 |

EXAMPLES 6 TO 10

The starting material for the following examples is [1S-(1α,2β(5Z),3β,4α)]-7-[3-(hydroxymethyl)-7-oxabicyclo[2.2.1]hept-2-yl]-5-heptenoic acid, methyl ester, which is prepared as described in U.S. Pat. No. 4,143,054, column 9, Example 7. This compound may be treated following the procedures of Example 1, parts H to L and Examples to 5 to form the following examples:

6. [1S-(1α,2α,3α,4α)]-2-[3-[3-[[(4-Cyclohexylbutyl)amino]carbonyl]-1,2,4-oxadiazol-5-yl]-7-oxabicyclo[2.2.1]hept-2-yl]-5-heptenoic acid, methyl ester;

7. [1S-(1α,2α,3α,4α)]-2-[3-[3-[[(4-Cyclohexylbutyl)aminocarbonyl]-1,2,4-oxadiazol-5-yl]-7-oxabicyclo[2.2.1]hept-2-yl]-5-heptenoic acid;

8. [1S-(1α,2α,3α,4α)]-2-[3-[3-[[(4-Cyclohexylbutyl)amino]carbonyl]-1,2,4-oxadiazol-5-yl]-7-oxabicyclo2.2.1]hept-2-yl]-5-heptenoic acid;

9. [1S-(1α,2α,3α,4α)]-2-[3-5-[[(4-Cyclohexylbutyl)amino]carbonyl]-1H-1,2,4-triazol-3yl]-7-oxabicyclo[2.2.1]hept-2-yl]-5-heptenoic acid, methyl ester; and 10. [1S-(1α,2α,3α,4α)-2-[3-5-[[(4-Cyclohexylbutyl)amino]carbonyl]-1H-1,2,4-triazol-3yl]-7-oxabicyclo[2.2.1]hept-2-yl]-5-heptenoic acid.

What is claimed is:

1. A compound having the formula and all stereoisomers and pharmaceutically acceptable salts thereof, wherein:

m is 1, 2, or 3;

n is 0, 1, 2 or 3;
R is $CO_2R'$, $CH_2OH$, $CONHSO_2R^3$, $CONHR^4$, or $-CH_2$-5-tetrazolyl;
R' is hydrogen, alkyl, or alkali metal;
X is O or NH;
Y is —O—, a single bond or vinylene, except that Y cannot be —O— when n is 0 and if Y is vinylene, then n=0;
Z is —CH=CH—, —(CH$_2$)$_2$— or;

$R^1$ is hydrogen, alkyl, alkenyl, alkynyl, aralkyl, aryl, cycloalkyl, cycloalkylalkyl, cycloheteroalkyl, cycloheteroalkylalkyl, heteroaryl or heteroarylalkyl, or amide, each of $R^1$ being unsubstituted or optionally substituted with alkyl, aryl, cycloalkyl, or cycloalkylalkyl;
$R^2$ is hydrogen, alkyl, aryl, or aralkyl;
$R^3$ is alkyl, aryl or aralkyl;
$R^4$ is hydrogen, alkyl, aryl or aralkyl
"alkyl" refers to groups of up to 12 carbon atoms;
"cycloalkyl" refers to saturated cyclic hydrocarbon groups of 3 to 12 carbon atoms;
"aryl" or "Ar" refers to phenyl and naphthyl, optionally substituted with 1 or 2 groups selected from alkyl, trifluoromethyl, halogen, alkoxy, hydroxy, alkylthio, alkylsulfinyl, alkylsulfonyl, phenylthio, phenylalkoxy, phenylsulfinyl, and phenylsulfonyl;
"alkenyl" and "alkynyl" refer to groups of up to 12 carbon atoms;
"cycloheteroalkyl" refers to 5-, 6- or 7-membered saturated rings having 1 to 2 heteroatoms selected from nitrogen, oxygen and sulfur that are linked through a carbon atom either beta or gamma to a heteroatom; and
"heteroaryl" refers to 5- or 6-membered aromatic rings having 1 or 2 heteroatoms selected from nitrogen, oxygen, and sulfur that are linked through a ring carbon atom.

2. A compound of the formula

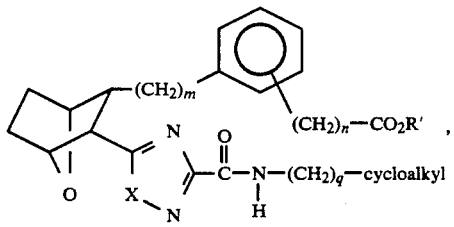

and all stereoisomers and pharmaceutically acceptable salts thereof, wherein:
q is an integer from 1 to 7;
m is 1, 2, or 3;
n is 0, 1, 2, or 3;
R' is hydrogen, alkyl, or alkali metal;
X is O or NH;
"alkyl" refers to groups of up to 12 carbon atoms; and
"cycloalkyl" refers to saturated cyclic hydrocarbon groups of 3 to 12 carbon atoms.

3. The compound of claim 1, wherein m is 1.
4. The compound of claim 2, wherein m is 1.
5. The compound of claim 2, wherein q is 4.
6. The compound of claim 1, wherein n is 2.
7. The compound of claim 2, wherein n is 2.
8. The compound of claim 1, wherein R is $CO_2R'$.
9. The compound of claim 2, wherein R' is hydrogen.
10. The compound of claim 8, wherein R' is hydrogen.
11. The compound of claim 2, wherein the cycloalkyl group is cyclohexane.
12. The compound of claim 1, wherein Z is

13. The compound of claim 1, wherein Z is the cis double bond isomer of —CH=CH—.
14. The compound of claim 1, selected from the group consisting of
[1S-(1α,2α,3α,4α)]-2-[[3-[3-[(4-Cyclohexylbutyl)aminocarbonyl]-1,2,4-oxadiazol-5-yl]-7-oxabicyclo[2.2.1]hept-2-yl]methyl]benzenepropanoic acid, methyl ester;
[1S-(1α,2α,3α,4α)]-2-[3-[3-[[(4-Cyclohexylbutyl)amino]carbonyl]-1,2,4-oxadiazol-5-yl]-7-oxabicyclo[2.2.1]hept-2-yl]methyl]benzenepropanoic acid;
[1S-(1α,2α,3α,4α) -2-[[3-[3-[[(4-Cyclohexylbutyl)amino]carbonyl]-1,2,4-oxadiazol-5-yl]-7oxabicyclo[2.2.1]hept-2-yl]methyl]benzenepropanoic acid;
[1S-(1α,2α,3α,4α)]-2-[3-[5-[(4-Cyclohexylbutyl)amino]carbonyl]-1H-1,2,4-triazol-3-yl]-7-oxabicyclo[2.2.1]hept-2-yl]methylbenzenepropanoic acid, methyl ester;
1S-(1α,2α,3α,4α)]-2-[[3-[5-[[(4-Cyclohexylbutyl)amino]carbonyl]-1H-1,2,4-triazol-3-yl]-7-oxabicyclo[2.2.1]hept-2-yl]methyl]benzenepropanoic acid;
1S-(1α,2α,3α,4α)]-2-[3-[3-[[(4-Cyclohexylbutyl)amino]carbonyl]-1,2,4-oxadiazol-5-yl]-7-oxabicyclo[2.2.1]hept-2-yl]-5-heptenoic acid, methyl ester;
1S-(1α,2α,3α,4α)]-2-[3-[3-[[(4-Cyclohexylbutyl)amino]carbonyl]-1,2,4-oxadiazol-5-yl]-7-oxabicyclo[2.2.1]hept-2-yl]-5-heptenoic acid;
1S-(1α,2α,3β,4α)]-2-[3-[3-[[(4-Cyclohexylbutyl)amino]carbonyl]-1,2,4-oxadiazol-5-yl]-7-oxabicyclo[2.2.1]hept-2-yl]-5-heptenoic acid;
1S-(1α,2α,3α,4α)]-2-[3-[5-[[(4-Cyclohexylbutyl)amino]carbonyl]-1H-1,2,4-triazol-3-yl]-7-oxabicyclo[2.2.1]hept-2-yl]-5-heptenoic acid, methyl ester; and
1S-(1α,2α,3α,4α)]-2-[[3-[5-[[(4-Cyclohexylbutyl)amino]carbonyl]-1H-1,2,4-triazol-3-yl]-7-oxabicyclo[2.2.1]hept-2-yl]-5-heptenoic acid.

15. A method of inhibiting platelet aggregation, which comprises administering to a mammalian host an effective amount of a compound as define din claim 1.
16. A method of inhibiting bronchoconstriction associated with asthma, which comprises administering to a mammalian host an effective amount of a compound as defined in claim 1.
17. A method of improving post-ischemic myocardial function, which comprises administering to a mammalian host in need of such treatment an effective amount of a compound as defined in claim 1.
18. A method for preventing or reducing venous thrombosis, which comprises administering to a mammalian host in need of such treatment an effective amount of a compound as defined in claim 1.

19. A method for preventing or reducing platelet loss during extracorporeal circulation, which comprises administering to a mammalian host in need of such treatment an effective amount of a compound as defined in claim 1.

20. A method for reducing post-ischemic myocardial injury, which comprises administering to a mammalian host in need of such treatment an effective amount of a compound as defined in claim 1 and an effective amount of a thrombolytic agent within 6 hours of a myocardial infarction.

* * * * *